United States Patent [19]

Blindheim et al.

[11] Patent Number: 4,567,313

[45] Date of Patent: Jan. 28, 1986

[54] METHOD FOR ISOMERIZING ALKYLBENZENES

[75] Inventors: Ulf Blindheim, Skedsmokorset; Gerd S. Haegh, Rykkin; Bjørn P. Nilsen, Sola, all of Norway

[73] Assignee: Sentralinstitutt for industriell forskning, Oslo, Norway

[21] Appl. No.: 616,184

[22] PCT Filed: Sep. 26, 1983

[86] PCT No.: PCT/NO83/00036
§ 371 Date: May 31, 1984
§ 102(e) Date: May 31, 1984

[87] PCT Pub. No.: WO84/01375
PCT Pub. Date: Apr. 12, 1984

[30] Foreign Application Priority Data

Oct. 1, 1982 [NO] Norway .................................. 823311

[51] Int. Cl.$^4$ .......................... C07C 5/22; C07C 5/23; C07C 5/25
[52] U.S. Cl. .................................. 585/480; 585/665; 585/670; 585/482
[58] Field of Search ............... 585/665, 670, 480, 482, 585/481

[56] References Cited

U.S. PATENT DOCUMENTS

| | | | |
|---|---|---|---|
| 3,078,318 | 2/1963 | Berger | 260/668 |
| 3,377,400 | 4/1968 | Wise | 260/668 |
| 3,381,048 | 4/1968 | Lovell et al. | 260/668 |
| 3,409,685 | 11/1968 | Donaldson et al. | 260/668 |
| 3,538,173 | 11/1970 | Berger et al. | 260/668 |
| 3,652,697 | 3/1972 | Hayes | 260/668 A |
| 3,879,484 | 4/1975 | Pollitzer | 260/668 A |
| 3,898,297 | 8/1975 | Sampson et al. | 260/668 A |
| 3,997,618 | 12/1976 | Cornely et al. | 260/668 A |
| 4,179,581 | 12/1979 | Mitsche et al. | 585/744 |

FOREIGN PATENT DOCUMENTS

| | | |
|---|---|---|
| 2057839 | 6/1971 | Fed. Rep. of Germany . |
| 2355312 | 5/1974 | Fed. Rep. of Germany . |
| 2511434 | 9/1975 | Fed. Rep. of Germany . |
| 2626195 | 1/1977 | Fed. Rep. of Germany . |
| 2742235 | 5/1978 | Fed. Rep. of Germany . |
| 2206124 | 8/1976 | France . |
| 2264796 | 12/1976 | France . |
| 1329140 | 9/1973 | United Kingdom ................ 585/665 |

OTHER PUBLICATIONS

Krzywicki et al., J. Chem. Soc. Faraday I, 1980, 76, 1311–1322.

Primary Examiner—John Doll
Assistant Examiner—Chung K. Pak
Attorney, Agent, or Firm—Wenderoth, Lind & Ponack

[57] ABSTRACT

A method of isomerizing alkylbenzenes, in particular xylenes. The method is based on the application of a catalyst which comprises an inorganic oxide support containing at least one mixed oxide compound of $SiO_2$ and $Al_2O_3$ in any proportion, and performing the isomerization at a temperature between 150° and 300° C. under a pressure ranging from about atmospheric to a few atmospheres. The catalyst is produced by reaction of the support with an aluminum alkyl compound of the type $AlR_yX_{3-y}$, wherein $R=CH_3$, $C_2H_5$ or $C_3H_7$, $y=1$ or 2 and $X=Cl$, preferably $Al(C_2H_5)Cl_2$. The support may be impregnated with platinum and/or rhenium. Characteristic features of this method are that the isomerization process can be run without any promotor, and that isomerization of xylene under moderate conditions yields a high degree of conversion and high selectivity. The process can be run with from 0 to 30% ethylbenzene in the feed stock and with or without dilution of the feed with toluene. The method is particularly applicable to converting meta-xylene to ortho- and para-xylene.

9 Claims, No Drawings

METHOD FOR ISOMERIZING ALKYLBENZENES

The present invention relates to a process for isomerizing alkylbenzenes, in particular xylenes, in the presence of a solid (heterogeneous) catalyst.

Aromatic $C_8$-fractions from petrochemical industrial plants and petroleum refineries will as a rule contain the three xylene-isomers in proportions which approximately are 18 percent ortho-xylene, 58 percent meta-xylene and 24 percent para-xylene. Meta-xylene is a substantially less demanded product than ortho- and para-xylene which i.a. constitute basic materials for important products such as phtalic acid anhydride and terephthalic acid. Consequently, conversion of meta-xylene to ortho- and para-xylene represents an important industrial process.

A previously well known and applied process for isomerization of xylenes relates to the use of a catalyst which is based on platinum deposited on the mixed oxide compound $SiO_2/Al_2O_3$. The process runs at temperatures from 420° to 480° C. and at pressures from 10 to 20 atm. The feed has a hydrogen/hydrocarbon ratio of approximately 10, and may contain up to 45 percent ethylbenzene.

In another previously known and applied xylene isomerization process a catalyst with platinum on $Al_2O_3$ is used. The conditions in this process are approximately as given above, except for a somewhat lower hydrogen consumption, and the feed may contain from 10 to 15 percent ethylbenzene.

More processes of similar types are utilized for isomerizing xylene. A common feature of these industrial processes is that they concern application of catalysts which comprise metal on supports, often platinum on $Al_2O_3$ or platinum on $SiO_2/Al_2O_3$.

In still another applied process for isomerizing xylene a zeolite catalyst containing rare earth metals is used. The process is a liquid phase process that runs at temperatures from 200° to 600° C. and at a pressure of 22 atm., and with 20 percent toluene in the feed.

In the patent literature isomerization of xylene by means of catalyst systems with platinum deposited on $Al_2O_3$ has been described (U.S. Pat. No. 4,179,581), systems with fluorided $Al_2O_3$ (U.S. Pat. No. 3,898,297). Catalyst systems with nickel deposited on $Al_2O_3$ and other oxide supports have also been described. Additionally, there are patent specifications relating to isomerization of xylene in the presence of different synthetic zeolite catalysts, as well as special liquid phase systems, for instance with $HF/BF_3$.

Conversion of meta-xylene to ortho-xylene and para-xylene is a monomolecular reaction which is assumed to go via 1,2-shifts of methyl groups. This reaction is independent of the pressure. On the contrary, bireactions, like e.g. disproportionation of xylene, are bimolecular reactions and are promoted by high pressure. These reactions consume more energy, and are more predominant at higher temperatures. Previously known processes applied industrially for isomerizing xylene are encumbered with the drawback that they are operated at relatively high pressures and temperatures, and thus yield unwanted by-products.

An object of the present invention is to provide a catalytic process for isomerizing alkylbenzenes at moderate pressures and temperatures in order to enhance the selectivity.

This object has been obtained by the method according to the invention, which method is based on the application of a heterogeneous catalyst which comprises an inorganic oxide support containing at least one mixed oxide compound of $SiO_2$ and $Al_2O_3$ in any proportion, and which is characterized in that the isomerization is performed at a temperature between 150° and 300° C. and under a pressure ranging from about atmospheric to a few atmospheres in the presence of a catalyst having been produced by reaction of the support with an aluminum alkyl compound of the type $AlR_yX_{3-y}$, wherein $R = CH_3$, $C_2H_5$ or $C_3H_7$, $y=1$ or 2 and $X = Cl$. The improved effect of the catalyst containing a mixed oxide compound of $SiO_2$ and $Al_2O_3$ is illustrated in table 1, below.

A catalyst with such an aluminum alkyl compound is known previously from DE Patent Application No. 2,626,195, but the catalyst described therein comprises a support consisting of aluminum oxide and boron oxide for quite another process, namely alkylation of aromatic hydrocarbons.

Further, another catalyst with such an aluminum alkyl compound is known previously from FR Patent Specification No. 2,264,796, but the catalyst described in some detail in this specification and as exemplified consists of aluminum oxide with noble metals and is applied for trans alkylation of toluene with polymethylbenzenes to produce xylenes.

Still further, patent specifications and other publications have been issued on aliphat-isomerization in the presence of aluminum sesqui-chloride deposited on $Al_2O_3$ impregnated with platinum, (FR Patent Specification No. 2,206,124. Research results on isomerization of the aliphatics butane and hexane in the presence of catalysts produced by depositing $Al(CH_3)Cl_2$ on aluminum oxide have been reported by A. Krzywicki, M. Marczewski, J.C.S. Faraday I, 1980, 76, 1311–1322.

The new catalyst given above and the production of this catalyst is of decisive importance for practical working of the invention, and partly for the understanding of the invention as well. Thus, the following description of the invention will also comprise a description of the catalyst and the production thereof. One characterizing feature of this production is that unreacted Al reagent can be removed after the reaction of the support with the aluminum alkyl compound by washing the product with a polar solvent, for instance chlorobenzene. This feature implies a considerable advantage over known processes because aluminum alkyl compounds under given circumstances may be present as strongly adsorbed dimer-like compounds on the surface of the catalyst, and it is of importance to the stability of the catalyst that adsorbed species be removed.

The materials of the support which were found to be well applicable for the production of the catalyst according to the invention are e.g. $SiO_2/13\%Al_2O_3$ and $Al_2O_3/6\% SiO_2$. The oxides were subjected to heat treatment (calcination) in the temperature range from 200° to 600° C., preferably 300° to 450° C., and reacted under inert conditions with aluminum alkyl compounds as given above, preferably with aluminum-ethyl-dichloride, $Al(C_2H_5)Cl_2$.

The reaction can take place in a separate reaction vessel or in the isomerization reactor to be used, in an atmosphere free from air or moisture, for instance under nitrogen or argon. A hydrocarbon solvent, preferably of the type $C_nH_{2n+2}$, wherein $n=5$, 6 or 7, is used as a reaction medium and/or solvent for the Al-compound.

Most expediently the conversion takes place at room temperature, and the product is dried in vacuum for several hours.

Al- and Cl-analyses suggest that reactions are taking place between the aluminum alkyl compound and hydroxyl groups on the surface of the support, such reactions being of the type:

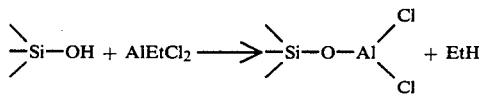

and:

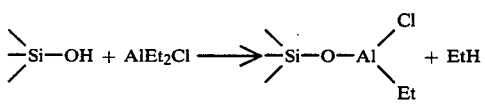

wherein $Et=C_2H_5$.

The amount of chlorine in the catalyst can be from 0.1 to 15 wt. percent, and preferably 3 to 12 wt. percent.

The catalyst can be subjected to heat treatment under inert conditions, separately or in the reactor, at temperatures in the range from 200° to 500° C., or if desired be calcined in an atmosphere with a controlled content of $H_2O$.

Prior to the reaction given above materials for the support can be impregnated with a metal compound, for instance an aqueous solution of $H_2PtCl_6$ and/or $NH_4ReO_4$.

In succession to such impregnation the impregnated product is reduced in a hydrogen atmosphere at temperatures in the range from 200° to 400° C. An impregnated support can contain from 0.1 to 2 percent Pt and/or Re, preferably 0.2 to 1 percent.

The isomerization process according to the invention is particularly well applicable to conversion of meta-xylene to ortho-xylene and para-xylene.

This isomerization process can be performed in gas or liquid phase, and as mentioned in the temperature range from 150° to 300° C. and at a pressure of about atmospheric to a few atmospheres. The feed can consist of meta-xylene or a mixture of $C_8$-aromatics where the ratio between the xylene isomers is different from that of an equilibrium mixture, and where the content of ethyl benzene can range from 0 to 30 percent. Thus it has been found that xylene can be isomerized under moderate conditions with a high degree of conversion and with very high selectivity. One characterizing feature of this isomerization process is that it can be run without addition of a promotor, contrary to the previously known processes wherein catalysts based on aluminum alkyl are applied, which processes seem to be conditioned by the use of a promotor in the feed stock, for instance use of the corrosive HCl.

The feed can be diluted with a solvent, and it has been found that dilution with up to 50 percent toluene gave a substantially improved selectivity, so that the selectivity in several cases amounted to approximately 100 percent. The effect on the degree of conversion as well was favourable in a number of occasions, and in no case negative.

The isomerization process has been run with or without hydrogen. When run with hydrogen the ratio hydrocarbon/$H_2$ = 1.

In liquid phase tests in an autoclave at a pressure of a few atmospheres and at a moderate temperature of 175° C. and with a meta-xylene/toluene ratio equalling 1 a maximum conversion and selectivity was obtained, i.e. conversion until the equilibrium ratio between the xylenes was achieved, and without formation of undesired by-products. An advantage of being able to operate at such mild conditions as set forth herein is that bireactions, as for instance disproportionation of xylene, are less pronounced. One of the disproportionation products is toluene, and industrial application of toluene as a solvent will also reduce this bireaction and contribute to high selectivity.

Gas phase tests in a fixed bed integral reactor showed that variants of catalysts as given above possessed a good stability after a certain initial phase, and that the stability was improved by introducing metal—in particular platinum—in the support. Presence of ethyl benzene in the feed had a low influence on the degree of isomerization and gave a small decrease in the selectivity. Hydrogen in the feed gave increased stability, and with hydrogen the selectivity was very high.

Table 1 below shows results from some examples of isomerization tests performed in accordance with the invention, with different feed compositions and with catalysts produced by reacting $AlEtCl_2$ with different types of supports. All catalysts were subjected to heat treatment at 250° C. prior to testing.

To present a survey, results have been given in table 2 below, which results show how low the conversion is in isomerization tests with $AlEtCl_2$ in homogeneous solution, and with pure, not chemically modified supports. As mentioned above, mixed oxide compounds of the type $Al_2O_3/SiO_2$ are applied as catalysts in commercial isomerization processes, but where the pressures and temperatures are substantially higher than those given by the invention. The test results show that the high selectivity and conversion which have been obtained in the isomerization process described herein, explicitly can be referred to the solid catalyst preparation, and not to soluted aluminum alkyl species, neither to effects of the support.

TABLE 1

| | Isomerization of meta-xylene in autoclave at 175° C. for 20 hours over solid catalysts based on $AlEtCl_2$. | | | | | |
|---|---|---|---|---|---|---|
| | | | | Feed | | |
| Type of support | Conversion % | Relative conversion % | Selectivity mol % | Meta-xylene mol % | Toluene mol % | Ethylbenzene mol % |
| SiO | 14.4 | 32.7 | 80.- | 100.- | | |
| $Al_2O_3$ | 23.7 | 53.3 | 82.4 | 100.- | | |
| 0.3% Pt/$Al_2O_3$ | 11.3 | 25.7 | 80.9 | 100.- | | |
| 0.3% Re/$Al_2O_3$ | 11.3 | 25.7 | 81.6 | 100.- | | |
| 0.3% Pt/0.2% Re/$Al_2O_3$ | 12.- | 27.3 | 84.- | 100.- | | |

TABLE 1-continued

Isomerization of meta-xylene in autoclave at 175° C. for 20 hours over solid catalysts based on AlEtCl$_2$.

| Type of support | Conversion % | Relative conversion % | Selectivity mol % | Feed Meta-xylene mol % | Toluene mol % | Ethyl-benzene mol % |
|---|---|---|---|---|---|---|
| Al$_2$O$_3$/6% SiO$_2$ | 26.7 | 70.7 | 78.7 | 100.- | | |
| SiO$_2$/13% Al$_2$O$_3$ | 31.4 | 71.4 | 82.4 | 100.- | | |
| " | 33.7 | 76.6 | ~100.- | 50.- | 50.- | |
| " | 38.2 | 86.8 | 92.1 | 75.- | 25.- | |
| " | 35.2 | 80.- | 90.4 | 90.- | 10.- | |
| SiO$_2$/12% Al$_2$O$_3$ | 33.3 | 87.- | 81.7 | 100.- | | |
| " | 41.1 | 93.4 | 92.3 | 50.- | 50.- | |
| " | 34.3 | 79.3 | 77.4 | 99.- | | 1.- |
| " | 40.- | 90.9 | 66.- | 95.- | | 5.- |
| " | 42.2 | 95.9 | 55.1 | 90.- | | 10.- |
| 0.3% Pt/SiO$_2$/12% Al$_2$O$_3$ | 35.- | 79.5 | 80.6 | 100.- | | |
| 0.4% Pt/SiO$_2$/12% Al$_2$O$_3$ | 42.2 | 95.9 | 75.9 | 100.- | | |
| 0.3% Re/SiO$_2$/12% Al$_2$O$_3$ | 34.9 | 79.3 | 81.6 | 100.- | | |
| 0.3% Pt/0.2% Re/12% Al$_2$O$_3$ | 35.2 | 80.- | 84.1 | 100.- | | |

Conversion = converted meta-xylene in percent (%).
Relative conversion = conversion in relation to maximum obtainable conversion (44%) under equilibrium conditions at 175° C.
Selectivity = percent (%) (ortho-xylene + para-xylene) in the product formed.

TABLE 2

Isomerization of meta-xylene in autoclave at 175° C./20 hours.

| Catalyst component | Conversion % | Relative conversion % | Selectivity % |
|---|---|---|---|
| AlEtCl$_2$ (solution) | 1.6 | 4.- | 88.- |
| SiO$_2$/400° C. | ~0 | ~0 | — |
| Al$_2$O$_3$/400° C. | 1.0 | 2.5 | 86.- |
| Al$_2$O$_3$/6% SiO$_2$/400° C. | 0.9 | 2.5 | 84.- |
| SiO$_2$/13% Al$_2$O$_3$/400° C. | 1.6 | 4.- | 63.- |

The invention is now explained by means of the following examples of, wherein Et=C$_2$H$_5$.

PRODUCTION OF CATALYST

Example 1

Reaction of SiO$_2$/13%Al$_2$O$_3$ (calcined at 400° C.) with AlEtCl$_2$ 15 g of a water-treated, calcined support SiO$_2$/12%Al$_2$O$_3$/400° C. were weighed out and transferred to an argon filled 250 ml two-necked flask connected to an inert gas line. 40 ml of absolute (abs.) normal (n-) hexane was added, and then a hexane solution of 15 ml 50% AlEtCl$_2$ was added. Heat and gas developed on adding AlEtCl$_2$; the reaction was rather vigorous the first 10 to 15 min., then the reaction subsided rapidly. After a respite for two hours at room temperature the mixture was transferred to a filter and the liquid was sucked off. The solid material was then washed with 2×25 ml of heptane and thereafter with chlorobenzene for 2 hours (6×25 ml), and finally with heptane (5×25 ml) for 1 hour. The solid material was dried 1 hour in vacuum (approx. 1 mm Hg), and thereafter 20 hours in high vaccum (approx. 10$^{-4}$ mm Hg). The preparation was preserved under argon in a schlenk-tube.

Al analyses on the catalyst showed: 10.55% Al. Al analyses on the support: 6.78% Al. This corresponds to 1.76 mmoles of deposited Al per g of catalyst. Cl analysis: 12.6%=3.56 mmoles Cl/g of catalyst. Molar ratio Cl:Al=3.56:1.76=2.02.

Example 2

Reaction of SiO$_2$/13%Al$_2$O$_3$ (calcined at 400° C.) with aluminum-diethyl-chloride, AlEt$_2$Cl The catalyst was produced by reaction of 19 g of SiO$_2$/13%Al$_2$O$_3$/400° C. with 5.5 ml of AlEt$_2$Cl in 50 abs. n-heptane in accordance with the method described in Example 1.

Results of analyses:
Al: (Al$_{cat.}$-Al$_{support}$)=2.66%=0.99 mmoles of Al/g
Cl: 5.42%=1.53 mmoles of Cl/g
C: (C$_{cat.}$-C$_{support}$)=3.40%=2.83 mmoles of C/g
H: (H$_{cat.}$-consumed OH)=0.68%=6.78 mmoles of H/g
Al:Cl:C$_2$:H$_5$=1:1.5:1.9:1.4 (moles).

Approx. 10 g of the catalyst were weighed out in a quartz vessel in a drybox and transferred inertly to an oven wherein the catalyst was dried at 250° C. under N$_2$ for 4 hours, cooled and transferred to a schlenk-tube.

Results of analyses:
Al: 2.66%=0.99 mmoles of Al/g
Cl: 5.54%=1.56 mmoles of Cl/g
C: 2.30%=1.92 mmoles of C/g
H: 0.46%=4.56 mmoles of H/g
Al:Cl:C$_2$H$_5$=1:1.6:0.94 (moles).

Example 3

Reaction of Pt-SiO$_2$/12%Al$_2$O$_3$ with AlEtCl$_2$ 30 g of SiO$_2$/Al$_2$O$_3$ were placed in a beaker and admixed with 0.24 g of H$_2$PtCl$_6$.6H$_2$O dissolved in 50 ml of distilled water. After 2 hours the solution was evaporated to dryness on evaporation apparatus (ROTAVAPOR) at 100° C. and dried for 2 hours at 150° C. (drying chamber) and thereafter for 23 hours at 400° C. under N$_2$.

Analysis: 0.27% Pt.

The material was reduced with H$_2$ for 4 hours at 200° C.

The Pt-impregnated support was transferred to a 2-necked flask under inert conditions and admixed with 50 ml abs. n-heptane, and further treated as described in Example 1. Chlorine analysis: 7.69% Cl.

Example 4

Reaction of Re-Al$_2$O$_3$ (calcined at 350° C.) with AlEtCl$_2$ 50 g of Al$_2$O$_3$ were impregnated with 220 mg of NH$_4$ReO$_4$ dissolved in 36 ml of water. After 24 hours the water was evaporated on ROTAVAPOR, and the sample was reduced with hydrogen. During the reaction the temperature was increased 1° C./min. to 350° C., and then kept at 350° C. for 2 hours.

Re-analysis: 0.34% Re.

The preparation was reacted with AlEtCl$_2$ under inert conditions as described in Example 1.

Cl-analysis: 5.8% Cl.

Example 5

Reaction of Pt,Re-Al$_2$O$_3$ with AlEtCl$_2$ 50 g of Al$_2$O$_3$ were placed in a beaker and admixed with a solution of 0.5 g of H$_2$PtCl$_6$.6H$_2$O and 0.11 of NH$_4$ReO$_4$ in 36 ml of distilled water. After preservation at room temperature (without stirring) for 24 hours the water was evaporated on ROTAVAPOR at 50° to 60° C.

Analyses: 0.26% Pt, 0.17% Re.

The material was reduced as described in the preceding example.

Then 30.6 g of the impregnated support was reacted with AlEtCl$_2$ as described in Example 1.

Analysis: 5.71% Cl.

Example 6

Reaction of SiO$_2$ (calcined at 600° C.) with AlEt$_2$Cl 2.5 g of SiO$_2$ were treated with 1.3 ml of AlEt$_2$Cl in 25 ml of n-hexane under inert conditions as described in Example 1.

Analysis: 4.1% Al, 5.25% Cl, 4.05% C$_2$H$_5$ (ethane was liberated by treatment with a concentrated alkaline solution). Al:Cl:C$_2$H$_5$=0.98:1:1.02.

ISOMERIZATION

Example 7

Isomerization of meta-xylene is liquid phase (1 atm.)

2 g of the catalyst as produced in accordance with Example 1 (SiO$_2$/13%Al$_2$O$_3$/400° C./AlEtCl$_2$) were admixed with 30 ml of meta-xylene and transferred inertly to a 100 ml 2-necked flask with reflux condenser. The mixture was refluxed (at approx. 150° C.) for 31 hours and samples were taken out with a syringe for gas chromatography (GC) analyses, at first taken every hour for 6 hours, then after a period of 23 hours, after another period of 26 hours and after a final one of 31 hours. On completing the test the catalyst was filtered off (inertly), washed with benzene and heptane, dried in vacuum and analysed for Cl. 5 ml of the filtrate were evaporated in air. The residue from the evaporation was diluted with acid and analysed for Al.

Results of analyses:
Catalyst before application: 3.4 mmoles of Cl/g
Catalyst after application: 3.4 mmoles of Cl/g Reaction mixture (liquid): Al was not detected, i.e. maximum 0.001 mmoles of Al/g was removed from the catalyst.

Product compositions:

| Reaction time hours | Products, mol % | | | | | |
|---|---|---|---|---|---|---|
| | toluene | benzene | p-X* | m-X* | c-X* | trimethyl benzene |
| 1 | 0.299 | 0.024 | 7.508 | 86.464 | 5.483 | 0.222 |
| 2 | 0.669 | — | 11.491 | 79.041 | 8.256 | 0.543 |
| 3 | 1.252 | 0.021 | 13.863 | 73.586 | 10.079 | 1.199 |
| 4 | 1.647 | 0.019 | 14.756 | 71.062 | 10.864 | 1.651 |
| 5 | 2.207 | 0.026 | 15.626 | 68.543 | 11.534 | 2.063 |
| 6 | 2.346 | 0.021 | 15.741 | 67.886 | 11.715 | 2.292 |
| 23 | 5.263 | 0.027 | 17.382 | 58.720 | 13.525 | 5.084 |
| 26 | 5.268 | 0.019 | 17.451 | 58.368 | 13.619 | 5.276 |
| 31 | 6.699 | 0.030 | 17.313 | 57.895 | 13.198 | 4.865 |

*p = para, m = meta, o = ortho, X = xylene, (As well as in the following description.)

Example 8

Isomerization of o-xylene and m-xylene in mixture in liquid phase (autoclave, 175° C.)

(a) 1 g of the catalyst produced in accordance with Example 1 (SiO$_2$/13%Al$_2$O$_3$400° C./AlEtCl$_2$) was admixed with 15 ml of a mixture of xylenes (o-xylene:m-xylene=1:9), transferred inertly to a Parr autoclave and kept heated at 175° C. for 20 hours. On completing the test the mixture was filtered inertly. The composition of products in the liquid was analysed on a GC.

When it is mentioned in this example, and in successive examples, that the isomerization was performed in an autoclave it is to be understood in this connection that the isomerization was performed at a pressure of from about atmospheric to a few atmospheres.

The catalyst was dried in vacuum and analysed for Cl. 5 ml of the filtrate were transferred to a round flask and cooled with liquid N$_2$. Then 2 to 3 ml of water were added, and the flask was kept at room temperature until warmed. The mixture was shaken, well admixed with 2.5 ml of 1N H$_2$SO$_4$ and transferred to a 50 ml flask. The organic layer was removed by means of a pipette, the flask was filled with destilled water, and the solution was analysed for Cl and Al.

Analyses:
Catalyst before application: 3.4 mmoles of Cl/g
Catalyst after application: 2.9 mmoles of Cl/g
Filtered reaction mixture: No detectable amounts of Al and Cl, i.e. <0.001 mmoles of Cl/g and <0.001 mmoles of Al/g of catalyst dissolved in the liquid
Conversion: 45.76%
Selectivity: 61.46%
Yield: 28.16% (Maximum obtainable yield: 40%)
o-xylene:m-xylene:p-xylene=20.9:58.0:24.2 (Thermodynamic equilibrium ratio: 20.0:55.8:24.2)

(b) An isomerization test under such conditions and with such a mixture of xylenes as described in (a), but with 1 g of a catalyst having been produced by reaction of SiO$_2$ (calcined at 400° C.) with AlEtCl$_2$, followed by drying in vacuum (SiO$_2$/400° C./AlEtCl$_2$).
Conversion: 14.4%
Selectivity: 80.0%
Yield: 11.5%

(c) An isomerization test as described in (a), but with 1 g of a catalyst having been produced by reaction of Al$_2$O$_3$ (calcined at 400° C.) with AlEtCl$_2$, followed by drying in vacuum.

Conversion: 39.1%
Selectivity: 68.3%
Yield: 26.7%

Example 9

An isomerization test as described in Example 8 with 1 g of a catalyst having been produced in accordance with Example 4 (Re/Al$_2$O$_3$/350° C./AlEtCl$_2$ dried at 250° C.) and with 15 ml of m-xylene in a Parr autoclave for 20 hours at 250° C.

Example 10

(A preferred example of performance)

Isomerization of m-xylene diluted with toluene in liquid phase (175° C., autoclave)

An isomerization test as described in Example 8 with 1 g of a catalyst (SiO$_2$/13%Al$_2$O$_3$/400° C./AlEtCl$_2$, dried at 250° C.) produced in accordance with Example 1, the feed consisting of 15 ml of m-xylene and 15 ml of toluene. The process was run for 20 hours at 175° C.
Conversion: 33.7%
Selectivity: ~100%

Example 11

Isomerization of m-xylene in liquid phase with ethylbenzene and toluene in the feed stock (175° C., autoclave)

The isomerization test was performed as described in Example 8, in which test 1 g of SiO$_2$/12%Al$_2$O$_3$ (calcined at 400° C.) having been reacted with AlEtCl$_2$ and calcined at 250° C. was added to 30 ml of a feed consisting of 45% m-xylene, 45% toluene and 10% ethylbenzene.
Conversion: 49.6%
Selectivity: 68.4%
Converted ethylbenzene: 74.4%

Example 12

Isomerization of m-xylene in liquid phase with ethylbenzene in the feed stock (250° C., autoclave)

The isomerization test was performed as described in Example 8 with 1 g of SiO$_2$/12%Al$_2$O$_3$ calcined at 400° C., reacted with AlEtCl$_2$ and dried at 500° C. The catalyst was supplied with 15 ml of m-xylene admixed with 5% ethylbenzene, and the process was run at 250° C. for 20 hours.
Conversion: 35.1%
Selectivity: 62.7%
Converted ethylbenzene: 49.5%

Example 13

Isomerization of m-xylene in liquid phase in the presence of toluene and hydrogen (a) Reaction conditions:
WHSV (Weight hourly space velocity): 0.42 g of xylene/g of catalyst per hour
Temperature: 180° C.
Amount of catalyst: 10 g of Pt/SiO$_2$/12%Al$_2$O$_3$ calcined at 400° C., reacted with AlEtCl$_2$ and dried at 250° C.
Hydrogen: 20 ml/min.
Feed mixture:
  0.05 moles % of benzene
  55.29 moles % of toluene
  0.11 moles % of p-xylene
  44.33 moles % of m-xylene
  0.19 moles % of o-xylene The catalyst was weighed inertly, commingled with an equal amount in volume of 1 ml glass beads and transferred to the reactor under N$_2$. After heating to 180° C. the test was started, and a mixture of hydrogen, toluene and m-xylene was pumped in. The product was analysed on a gas chromatograph with an automatic gas sampling system. Samples were taken every hour, initially, later every two hours and then every four hours.

The conversion decreased slowly from approx. 50% in the initial phase to approx. 25% after 72 hours, and the selectivity increased from approx. 75% to approx. 90%.

(b) An isomerization test with conditions and feed stock as described in (a), but with 10 g of a catalyst having been produced by reacting Re/SiO$_2$/12%Al$_2$O$_3$ (hydrogenated at 350° C.) by means of the method described in Example 4.

The conversion decreased from 42% at start to 15% after 80 hours, and the selectivity increased in the same period of time from 70% to 86%.

(c) An isomerization test as described in (a), but with 10 g of a catalyst having been produced by reacting Pt,Re/SiO$_2$/12%Al$_2$O$_3$ (hydrogenated at 350° C.) with AlEtCl$_2$ followed by drying at 250° C. as described in Example 5.

The conversion decreased from 48% at start to 23% after 75 hours, and the selctivity increased in the same period of time from 72% to 83%.

(d) An isomerization test as described in (a), but with 10 g of a catalyst having been produced in accordance with Example 1 (SiO$_2$/12%Al$_2$O$_3$/400° C./AlEtCl$_2$) and dried at 250° C.

The conversion decreased from 40% at start to approx. 10% after 75 hours, and the selectivity increased in the same period of time from 78% to 95%.

Example 14

Isomerization of m-xylene in gas phase

An isomerization test performed as described in Example 13.
Catalyst: 10 g of SiO$_2$/12%Al$_2$O$_3$ calcined at 400° C., reacted with AlEtCl$_2$ and dried at 250° C.
Feed: m-xylene (98.28%)
Reaction temperature: 190° C.
WHSV: 0.21
Sampling: every 30 min.
Conversion 48.5 hours: 26.2% (85.3% selectivity)

|  | % Cl | % C | H |
|---|---|---|---|
| Analysis of catalyst before test: | 5.27 | 0.50 | 0.42 |
| Analysis of catalyst after test: | 4.93 | 3.92 | 0.58 |

Example 15

An isomerization test performed as described in Example 13

Catalyst: 10 g of Al$_2$O$_3$/6%SiO$_2$ calcined at 400° C., reacted with AlEtCl$_2$ and calcined at 250° C.
Feed: m-xylene
Reaction temperature: 183° C.
WHSV: 0.21
Sampling: every 30 min.
Maximum obtainable conversion: 75.8% after 1 hour
Conversion after 22 hours: 5.1%
Selectivity: 84.1%

Example 16

Isomerization of m-xylene in gas phase with ethylbenzene in the feed

An isomerization test as described in Example 13.
WHSV: 0.42
Temperature: 190° C.
Catalyst: 10 g of $SiO_2/12\%Al_2O_3$ calcined at 400° C., reacted with $AlEtCl_2$, and dried at 250° C.
Feed mixture:
 0.06 moles % of benzene
 0.68 moles % of toluene
 0.29 moles % of p-xylene
 93.64 moles % of m-xylene
 0.62 moles % of o-xylene
 4.69 moles % of ethylbenzene
Conversion after 20 hours: 14.9%
Selectivity after 20 hours: 86.3%

Example 17

Isomerization of m-xylene in gas phase

An isomerization test performed as described in Example 13.
WHSV: 0.28
Temperature: 190° C.
Catalyst: 10 g of $SiO_2$ calcined at 400° C., reacted with $AlEtCl_2$ and dried in vacuum at 20° C.
Feed: m-xylene
Conversion after 6 hours: 13.2%
Selectivity after 6 hours: 82.2%

We claim:

1. A method for isomerization of xylenes, which comprises contacting a feed comprising the xylenes, under isomerization conditions, with a heterogenous catalyst comprising an inorganic oxide support containing at least one mixed oxide compound of $SiO_2$ and $Al_2O_3$ at a temperature from 150° to 300° C. and under a pressure of at least about atmospheric pressure, wherein the catalyst is produced by reaction of the support with an aluminum alkyl compound of the formula $AlR_yX_{3-y}$ where R is $CH_3$, $C_2H_5$ or $C_3H_7$, y is 1 or 2, and X is Cl.

2. A method as claimed in claim 1, wherein the isomerization is performed in the presence of the catalyst where the support has been impregnated with at least one of the metal compounds $H_2PtCl_6$ and $NH_4ReO_4$ prior to the reaction of the support with the aluminum alkyl compound.

3. A method as claimed in claim 2 wherein the xylenes are subjected to the isomerization conditions in the presence of the catalyst produced by reaction of the support with the aluminium alkyl compound $Al(C_2H_5)Cl_2$.

4. A method as claimed in claim 1, wherein the xylenes are subjected to the isomerization conditions in the presence of the catalyst produced by reaction of the support with the aluminum alkyl compound $Al(C_2H_5)Cl_2$.

5. A method as claimed in claim 4 wherein the feed comprises meta-xylene and toluene in a ratio of 1:1 and is subjected to the isomerization conditions for conversion of meta-xylene to ortho-xylene and para-xylene.

6. A method as claimed in claim 1, wherein the feed comprises meta-xylene and toluene in a ratio of 1:1 and is subjected to the isomerization conditions for conversion of meta-xylene to ortho-xylene and para-xylene.

7. A method as claimed in claim 6, wherein hydrogen is supplied to the feed, so that the ratio hydrocarbon:hydrogen is 1:1.

8. A method as claimed in claim 6, wherein the feed contains from 0 to 30% ethylbenzene.

9. A method as claimed in claim 8, wherein hydrogen is supplied to the feed, so that the ratio hydrocarbon:hydrogen = 1:1.

* * * * *